United States Patent
Hanko

(10) Patent No.: US 8,625,100 B2
(45) Date of Patent: Jan. 7, 2014

(54) METHOD FOR THE OPTICAL DETERMINING OF A MEASURED VARIABLE OF A MEDIUM

(75) Inventor: Michael Hanko, Dresden (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 335 days.

(21) Appl. No.: 13/003,594

(22) PCT Filed: Jul. 7, 2009

(86) PCT No.: PCT/EP2009/058541
§ 371 (c)(1),
(2), (4) Date: Jan. 11, 2011

(87) PCT Pub. No.: WO2010/006950
PCT Pub. Date: Jan. 21, 2010

(65) Prior Publication Data
US 2011/0108739 A1 May 12, 2011

(30) Foreign Application Priority Data

Jul. 15, 2008 (DE) .......................... 10 2008 033 214

(51) Int. Cl.
*G01J 3/30* (2006.01)
*G01J 1/58* (2006.01)

(52) U.S. Cl.
USPC ....................................... 356/445; 250/459.1

(58) Field of Classification Search
USPC .......................................... 356/445; 436/133
See application file for complete search history.

(56) References Cited

U.S. PATENT DOCUMENTS 4,845,368 A 7/1989 Demas
5,485,530 A 1/1996 Lakowicz
(Continued)

FOREIGN PATENT DOCUMENTS

DE 43 20 038 C1 12/1994
(Continued)

OTHER PUBLICATIONS

Definition of "phase difference" from Collins English Dictionary online, printed Mar. 8, 2013.*

*Primary Examiner* — Gregory J Toatley
*Assistant Examiner* — Rebecca C Bryant
(74) *Attorney, Agent, or Firm* — Bacon & Thomas, PLLC

(57) ABSTRACT

In a method for determining a measured variable of a measured medium, wherein the measured medium is brought in contact with an indicator or an indicator mixture, whose absorption spectrum has a first, and a second, wavelength range, which essentially do not overlap, a first light source is activated for emitting a first light signal with a wavelength from the first wavelength range and a second light source is activated for emitting a second light signal with a wavelength from the second wavelength range. The intensity of the first light signal is modulated by a first and the intensity of the second light signal by a second, periodic signal, wherein at least a part of the first light signal and at least a part of the second light signal propagate as first and second measurement light signals along a measuring path and are transformed on the measuring path by optical interaction with the indicator or the indicator mixture to transformed measurement light signals, and wherein a total intensity of the transformed first and second measurement light signals is registered. The first periodic signal has a first phase difference relative to the second, periodic signal, and a second phase difference between the total intensity of the transformed first and second measurement light signals and the first, or the second, periodic signal is ascertained. The measured variable is determined with application of the second phase difference.

31 Claims, 5 Drawing Sheets

(56) References Cited

U.S. PATENT DOCUMENTS

| | | | |
|---|---|---|---|
| 5,530,709 A * | 6/1996 | Waarts et al. | 372/6 |
| 5,672,515 A | 9/1997 | Furlong | |
| 5,941,827 A * | 8/1999 | Papaioannou | 600/473 |
| 6,602,716 B1 | 8/2003 | Klimant | |
| 7,054,002 B1 * | 5/2006 | Sevick-Muraca et al. | 356/317 |
| 7,154,661 B2 | 12/2006 | Seah | |
| 2006/0257094 A1 | 11/2006 | McEvoy | |

FOREIGN PATENT DOCUMENTS

| | | |
|---|---|---|
| DE | 44 46 390 C1 | 7/1996 |
| DE | 103 35 114 A1 | 2/2005 |
| DE | 10 2005 062 910 A1 | 7/2007 |
| EP | 0 081 947 A1 | 6/1983 |
| EP | 0 702 226 A2 | 3/1996 |
| EP | 0 850 409 B1 | 7/1998 |
| EP | 1 743 576 A1 | 1/2007 |
| WO | WO 00/08443 | 2/2000 |
| WO | WO 02/40972 A1 | 5/2002 |
| WO | WO 02/056023 A1 | 7/2002 |
| WO | WO 2005/033746 A2 | 4/2005 |
| WO | WO 2008/097199 A1 | 8/2008 |

* cited by examiner a)

b)

METHOD FOR THE OPTICAL DETERMINING OF A MEASURED VARIABLE OF A MEDIUM

TECHNICAL FIELD

The invention relates to a method for the optical determining of a measured variable of a measured medium, wherein the measured medium is brought in contact with an indicator or an indicator mixture. The invention relates, furthermore, to an apparatus for performing this method.

BACKGROUND DISCUSSION

Such methods for the optical, especially photometric, determining of a pH value or a concentration of an analyte in the measured medium are known. Frequently, in such case, an indicator is used, whose absorption spectrum, or emission spectrum, as the case may be, in the case of excitation with a certain wavelength, changes as a function of the measured variable to be determined.

In the case of photometric determination of such measured variables, a number of disturbing factors can degrade the accuracy of measurement. For assuring a high accuracy of measurement, consequently, referencing the measurement signals is of great importance. From DE 103 16 685 A1, for example, a measuring apparatus for the photometric measuring of concentration of a chemical substance in a measured solution is known, in the case of which a transmitting unit produces electromagnetic radiation in at least two wavelength ranges and radiates into a cuvette containing the measured solution, wherein the electromagnetic radiation in a first wavelength range serves for measurement purposes and the electromagnetic radiation in a second wavelength range is taken into consideration for reference purposes. In such case, the electromagnetic radiation in both wavelength ranges takes the same path through the cuvette and the measured solution. This is achieved with a dual light emitting diode as light source, which is operated in such a manner, that it alternately transmits electromagnetic radiation in the two wavelength ranges. Disturbing influences, such as clouding of the measured solution or impurities dissolved in the measured solution, or refraction and reflection at interfaces, e.g. on windows, within the beam paths of both beams should be eliminated in this way.

From EP 850 409 B1, a method is known, in the case of which an analyte sensitive indicator brought in contact with the measured medium is excited simultaneously with activation of two modulated light signals of different wavelength. The wavelengths of the light signals are selected from two different regions of the excitation spectrum of the indicator, which are influenced by the concentration of the analyte to be detected in different manners. The corresponding signals emitted by the indicator are detected, demodulated and, from the intensity ratio of the demodulated emission signals, the concentration of the analyte is determined.

Such methods, in the case of which the ratio of the intensity of a signal influenced by the measured variable and the intensity of a signal not influenced, or influenced in different measure, by the measured variable is formed, are referred to as ratiometric methods. In the case of these methods, a lessening of the indicator concentration in the measuring path (a so-called washing out or "leaching") and a bleaching by photochemical reactions (so-called photobleaching or "bleaching") do not, due to the ratio formation between the intensities of the two signals, affect the measurement result.

Since, in the case of conventional ratiometry, the two signals are always separately registered, the known methods require two separated signal paths or else means, which permit a sequential registering of the signals. Alternatively, as described in EP 850 409 B1, the separation of the two signals can also occur by modulating the two radiated signals and then demodulating for the evaluation. This is associated with corresponding apparatus complexity and/or space requirements.

In the article "Dual wavelength referencing of optical fiber sensors" by G. Murtaza, J. M. Senior, Optics Communications, 120 (1995), Pgs. 348-357, the application of ratiometric methods in sensors with optical fibers is considered. In the article, it is noted that the measurement accuracy of the method is limited by the fact that two light signals of different wavelengths react in different manners to environmental influences, wherein especially two light signals of different wavelengths are transmitted in different measure by optical components. A quantifying of this effect or proposals for the solution of this problem are not given.

In EP 1000345 B1 and in the article "Dual Lifetime Referencing (DLR)—a New Scheme for Domain Information" in "New Trends in fluorescence spectroscopy: application to chemical and life science", B. Valeur, J.-C. Brochon (editors), Springer Verlag (publisher), Berlin Heidelberg 2001, Pgs. 257-274, a photometric method for determining a measured variable in a sample, especially the pH value or a concentration of an analyte, is given. In such case, two indicators are excited with a signal of a single wavelength to luminesce, wherein the luminescence intensity of the one indicator changes as a function of the measured variable, while the luminescence intensity of the other indicator, which serves as reference indicator, is not influenced by the measured variable. Moreover, the indicators are so selected, that the decay time of the luminescence of the reference indicator is significantly longer than that of the indicator influenced by the measured variable. If the intensity of the exciter signal is periodically modulated, there results, due to the different decay times between the two luminescence signal intensities of the measured value sensitive indicator and the reference indicator, a phase difference. The total intensity, i.e. the sum of the luminescence signals, has, relative to a reference (for example, the periodic exciter signal), a phase difference, which is dependent on the intensity ratio of the luminescence signals of the two indicators, and, thus, serves as a measure for the measured variable to be determined.

Through the application of a reference indicator, in the case of this method, in turn, disturbing influences can be eliminated. However, this method is only applicable for suitable combinations of luminescence-indicators, which can be excited with one and the same excitation wavelength and supplementally also possess a suitable relationship of the luminescence decay times, in order that a sufficient phase difference between the luminescence-signals is assured. Additionally, the measured signal is dependent on the concentration of the measuring, and the reference, indicator, or on their concentration ratio. In case one of the indicators is affected more strongly by leaching or bleaching, this leads to a degrading of the accuracy of measurement.

SUMMARY OF THE INVENTION

An object of the invention is to provide an optical method for determining a measured variable of a measured medium, as well as an apparatus for performing the method, which overcome the disadvantages of the state of the art. Especially, a method as well as an apparatus for performing the method should be given, which is, or are, universally applicable, both based on absorption, and on luminescence, measurements, as well as with a plurality of indicators, and can be embodied in small space with little apparatus complexity.

This object is achieved by a method for determining a measured variable of a measured medium, wherein the measured medium is brought in contact with an indicator or an indicator mixture, whose absorption spectrum has a first, and a second, wavelength range, which essentially do not overlap, wherein a first light source is activated for emitting a first light signal with a wavelength from the first wavelength range and a second light source is activated for emitting a second light signal with a wavelength from the second wavelength range, wherein the intensity of the first light signal is modulated by a first, and the intensity of the second light signal by a second, periodic signal,
wherein at least a part of the first and at least a part of the second light signals propagate as first and second measurement light signals along a measuring path and are transformed on the measuring path by optical interaction with the indicator or the indicator mixture, and
wherein a total intensity of the transformed first and second light signals is registered,
wherein the first periodic signal has a first phase difference relative to the second, periodic signal, and
a second phase difference between the total intensity of the transformed first and second measurement light signals and the first, or the second, periodic signal is ascertained,
and the measured variable is determined with application of the second phase difference.

The terminology "periodic signal" means a signal, which is describable as a periodic function, especially a function of time. The modulating of a such a signal on the intensity of a light signal leads correspondingly to a periodic change of the intensity of the light signal. If the intensity of a light signal is, for example, modulated with a signal describable with a sine function, the resulting modulated intensity of the light signal is displayable as a sine function. The terminology, "modulating the intensity of the first, and the second, light signal with a periodic signal" means, especially modulating with a periodic signal, which, in the case of addition of at least two of these periodic, even phase shifted, signals, advantageously yields, in turn, a periodic signal with the same signal form. Included, here, are especially trigonometric periodic signals, as, for example, a sine signal.

The measured medium can be, especially, a liquid or a gas. Both a single indicator, e.g. bromine thymol blue, can be used for determining the pH value as measured variable, as well as also an indicator mixture, which includes a plurality of indicators.

Since, instead of an intensity ratio of two signals, a phase difference of two periodic signals is determined, the apparatus complexity is less compared to the method known from the state of the art, as is explained below in connection with the examples of embodiments. Knowing the indicator concentration, from the phase difference between the periodically modulated, total intensity and the periodically modulated intensity of one of the single signals, e.g. the first or second light signal, the measured variable to be determined, e.g. the pH value, can be determined. For this method, only one detector is required, since the intensities of the transformed first and the transformed second measurement light signals do not need to be determined separately from one another, but, instead, only the periodically varying, total intensity of these two light signals is detected, in order to determine the phase difference between this total intensity and the first or second, periodic signal. Correspondingly, also no signal paths separated completely from one another need to be provided for the first and second measurement light signals, nor do the measurement light signals need to be separated from one another by demodulation techniques or by sequential registering. Of advantage, furthermore, is that the method of the invention is suitable both for absorption—as well as also for luminescence measurements. This enabled the application of a clearly expanded selection of indicators compared to the conventional method.

The second phase difference, i.e. the phase difference between the total intensity of the transformed first and second measurement light signals and the first, or the second, periodic signal modulating the intensity of the first or second light signal, can be determined e.g. by determining the phase difference between the intensity of the first measurement light signal and the total intensity of the transformed first and second measurement light signals, or the phase difference between the intensity of the second measurement light signal and the total intensity of the transformed first and second measurement light signals. This phase difference is the second phase difference.

Since the modulation frequency of the intensity of the individual measurement light signals is not changed by the interaction with the indicator or indicator mixture, the phase difference between the total intensity of the transformed measurement light signals and the non transformed first or second measurement light signal is identical with the phase difference between the total intensity of the transformed measurement light signals and the transformed first or second measurement light signal. In a method variant, therefore, the second phase difference can also be determined by measuring the phase difference between the intensity of the first transformed measurement light signal and the total intensity of the transformed first and second measurement light signals, or the phase difference between the intensity of the transformed second measurement light signal and the total intensity of the transformed first and second measurement light signals. In such case, however, additional means for detection of the intensities of the transformed measurement light signals are required, e.g. means such as demodulation techniques or additional detectors. Thus, is in the case of this method variant, the apparatus complexity is greater, compared with the variant described in the above paragraph. The remaining advantages of the method described here and in the following, especially the universal applicability of the method, as well as the increased accuracy of measurement described further below, combined with equal complexity compared with conventional ratiometric methods, are still obtained also in the case of this method variant.

In a first method embodiment, the absorption spectrum of the indicator or the indicator mixture is influenced by the measured variable to be determined in the first wavelength range and in the second wavelength range, wherein especially a change of the measured variable effects a different change of the absorption spectrum of the indicator or the indicator mixture in the first and in the second wavelength ranges.

The terminology, "a change in the absorption spectrum", means, here and in the following, an increase or decrease of absorption or transmission, at least within a limited wavelength range.

In a second method embodiment, the emission spectrum of the indicator or the indicator mixture is influenced by the measured variable to be determined as a function of whether excitation is in the first wavelength range or in the second wavelength range, wherein, especially, a change of the measured variable effects a different change of the emission spectrum of the indicator or of the indicator mixture, depending on whether excitation is in the first or in the second wavelength range.

The terminology, "a change of the emission spectrum, means, here and in the following, the increase or decrease of emission intensity in the case of excitation within a limited wavelength region.

In a third method embodiment, the absorption spectrum of the indicator or the indicator mixture is influenced in the first wavelength range by the measured variable to be determined and not in the second wavelength range by the measured variable to be determined influenced, wherein, especially, a change of the measured variable effects a change of the absorption spectrum in the first wavelength range and no change of the absorption spectrum in the second wavelength range.

In a fourth method embodiment, the emission spectrum of the indicator or the indicator mixture is influenced by the measured variable to be determined as a function of excitation in the first wavelength range and not influenced by the measured variable to be determined as a function of excitation in the second wavelength range, wherein, especially, a change of the measured variable effects a change of the emission spectrum as a function of excitation in the first wavelength range and no change of the emission spectrum as a function of excitation in the second wavelength range.

In a further development of the third or fourth method embodiments, the second wavelength range corresponds to an isosbestic point of the indicator or of the indicator mixture.

In a further development of all described method embodiments, the total intensity of the transformed first and second measurement light signals is registered with a single detector. This reduces the apparatus complexity compared with the method known from the state of the art.

In an additional embodiment, the intensity of the first, and the second, light signal is, in each case, modulated by a sine-like periodic signal. Advantageously, the first and/or the second sine-like periodic signal has a frequency of, for example, 500 Hz up to a plurality of megahertz (MHz). In contrast to the method described in EP 1000345 B1, in the case of which an analyte sensitive and an analyte insensitive reference indicator are excited with a single modulated exciter signal to luminesce, and from the phase shift the luminescence response of both indicators, the concentration of the analyte, or the pH value, is ascertained, and in the case of which the modulation frequency of the exciter signal must be selected as a function of the luminescence-decay times of the indicators, in the case of the here described method, the frequency of the first and second, periodic signal is freely selectable. This has the advantage, that the frequencies can be so selected, that apparatus complexity for the modulation of the periodic signals onto the intensity of the first and second light signal can be kept as small as possible.

Preferably, the first sine-like periodic signal modulated on the intensity of the first light signal and the second sine-like periodic signal modulated on the intensity of the second light signal have equal frequencies and a fixed phase difference, especially of 90° or π/2.

The intensity ratio of the first and of the second light signals, or the amplitude ratio of the intensities of the light signals correspondingly modulated with the first and second, periodic signals is freely selectable, while, however, preferably being held constant. Especially, the intensity ratio and/or the amplitude ratio can have the value 1.

The terminology, "a sine-like signal", means, here and in the following, a function of the form, $$F(t) = A_m \sin(2\pi f_m t - \phi),$$

wherein $f_m$ is the frequency of the sine-like signal, $A_m$ the amplitude of the sine-like signal and $\phi$ the phase shift of the sine-like signal.

In an embodiment of the method, especially when the intensities of the first and second light signals are modulated with a sine-like function, from the phase difference between the total intensity of the transformed first and second measurement light signals and the first, or second, periodic signal modulated on the first, or the second, light signal (earlier referred to as the second phase difference), the ratio of the amplitudes of the intensities of the transformed measurement light signals is ascertained.

In a further development of the method, supplementally to the phase difference between the total intensity of the transformed first and second measurement light signals and the first, or second, periodic signal modulated on the first, or the second, light signal (earlier referred to as the second phase difference), the amplitude of the total intensity of the transformed first and second measurement light signals is determined, and, therefrom, a ratio of absorption- or, alternatively, transmission values or a ratio of luminescence values of the transformed measurement light signals is ascertained. This has the advantage, that the indicator concentration is not relevant in determining the measured variable. The method is, thus, independent of a change of the indicator concentration during the course of the method, for example, due to leaching or bleaching.

In an additional embodiment, the first and second measurement light signals are changed on the measuring path by additional influences, especially in such a manner, that the intensities of the first and second measurement light signals are changed by the additional influences by different amounts, i.e., for example, lessened or increased in their intensities by different amounts, and wherein at least a further part of the first light signal emitted by the first light source as first reference light signal and at least a further part of the second light signal emitted by the second light source as second reference light signal are exposed on a reference path to the same influences, so that the intensity of the first and second reference light signals is, in each case, changed by the additional influences, wherein on the reference path the first, and the second, reference light signals are not allowed to interact with the indicator or the indicator mixture. In such case, the additional influences comprise especially fluctuations of the light intensity of the first and/or second light source, absorption and/or refraction of the light signals by substances in the measuring path and/or in the reference path, reflection on interfaces in the measuring path or a different sensitivity of the detector to the changed first and the changed second measurement light signals and/or the changed first and the changed second reference light signals or the incidence of ambient light.

In a method variant, the total intensity of the first and second changed reference light signal is registered with a detector, especially with an additional detector, and the phase difference between the total intensity of the changed first and second reference light signal and the first, or the second, periodic signal is ascertained and taken into consideration together with the phase difference between the total intensity of the transformed first and second measurement light signals and the first or second, periodic signal for determining the measured variable.

As earlier described for the signals of the measuring path, from the ascertained phase difference, an amplitude ratio of the intensities of the changed reference light signals or, when supplementally the amplitude of the total intensity of the changed first and second reference light signal is determined, a ratio of absorption values or of luminescence values of the changed reference light signals is ascertained.

In an alternative method variant, the intensity of the first light signal and the intensity of the second light signal are selected in such a manner relative to one another, that the phase difference between the total intensity of the changed first and second reference light signal and the first or second, periodic signal is constant. This has the advantage, that, in the case of determining the measured variable, no additional signals need be taken into consideration supplementally to the measurement light signals.

In the case of the described method embodiments and further developments, the measured variable can be the pH value of the measured medium or the concentration of an analyte contained in the measured medium, especially an analyte selected from the group consisting of carbon dioxide, oxygen, chlorine, hydrogen, ammonia, nitrate-, ammonium-, chloride-, fluoride-, phosphate-, sulfate-, cyanide-, alkali- and alkaline earth-ions, heavy metal containing ionic compounds and biomolecules, especially proteins or substances, which are produced by microorganisms.

The object is achieved, moreover, by an apparatus for performing the previously described method, comprising a first, and a second, light source for emitting a first, and a second, light signal, a matrix, which contains the indicator or the indicator mixture, and at least one detector for registering the total intensity of first and second measurement light signals transformed by optical interaction with the indicator or indicator mixture. The providing of an indicator embedded in a matrix permits a compact construction of the apparatus, so that, for example, the light sources and/or light conductor leading from the light sources to the matrix, the detector and/or light conductors leading from the matrix to the detector and the matrix can be components of a measuring probe immersible in the measured medium.

In a further development, the matrix includes, besides a first region, which contains the indicator or the indicator mixture, a second, indicator free region. This permits the implementing of a measuring path and a reference path in confined space.

In a further development, in each case, a measuring path for the first and second measurement light signals and a reference path for the first, and the second, reference light signals are provided,
wherein the measuring path comprises the first region of the matrix and the detector for registering the intensity of the measurement light signals transformed by optical interaction with the indicator or indicator mixture and by additional influences,
and the reference path comprises the second, indicator free region of the matrix and said detector or an additional detector for registering the intensity of the reference light signal changed only by the additional influences.

In a further development, the first, and the second, light source and the detector are arranged on the same side of the matrix. This contributes likewise to the compact construction of the apparatus, in order, for example, to accommodate them at least partially in a probe immersible in the measured medium.

In an embodiment, which is of advantage, especially, however, not only, for the case, in which the first, and the second, light source and the detector are arranged on the same side of the matrix, the matrix includes reflection amplifying means, especially a reflecting layer and/or light scattering particles integrated into the matrix.

In an embodiment, the first, and the second, light source are integrated in a dual light emitting diode. The bring together of both light sources into one component permits a still more compact construction of the apparatus.

In a further development, the apparatus furthermore includes an apparatus for producing the first phase difference, i.e. the phase difference between the first periodic signal modulating the light signal of the first light source and the second, periodic signal modulating the light signal of the second light source. Furthermore, the apparatus includes an apparatus for determining the second phase difference, i.e. the phase difference between the total intensity of the first and second measurement light signals transformed on the measuring path and the first or second, periodic signal, as well as the phase difference of the reference signal relative to the first, or the second, periodic signal. In a further development, the apparatus includes additional means for determining the amplitude of the total intensity of the first and second measurement light signals transformed on the measuring path.

The apparatus for determining the second phase difference can, for example, be so embodied, that it, in performing the described method, determines the phase difference between the (modulated) intensity of the first measurement light signal, or of the second measurement light signal, and the total intensity of the transformed first and second measurement light signals. The apparatus for determining the second phase difference can, in a variant, also be embodied in such a manner, that it, in performing the described method, determines the phase difference between the intensity of the first transformed measurement light signal, or of the second transformed measurement light signal, and the total intensity of the transformed first and second measurement light signals.

BRIEF DESCRIPTION OF THE DRAWINGS

In the following, the invention will now be explained on the basis of the drawing, the figures of which show as follows.

DETAILED DISCUSSION IN CONJUNCTION WITH THE DRAWINGS

Figure 1:
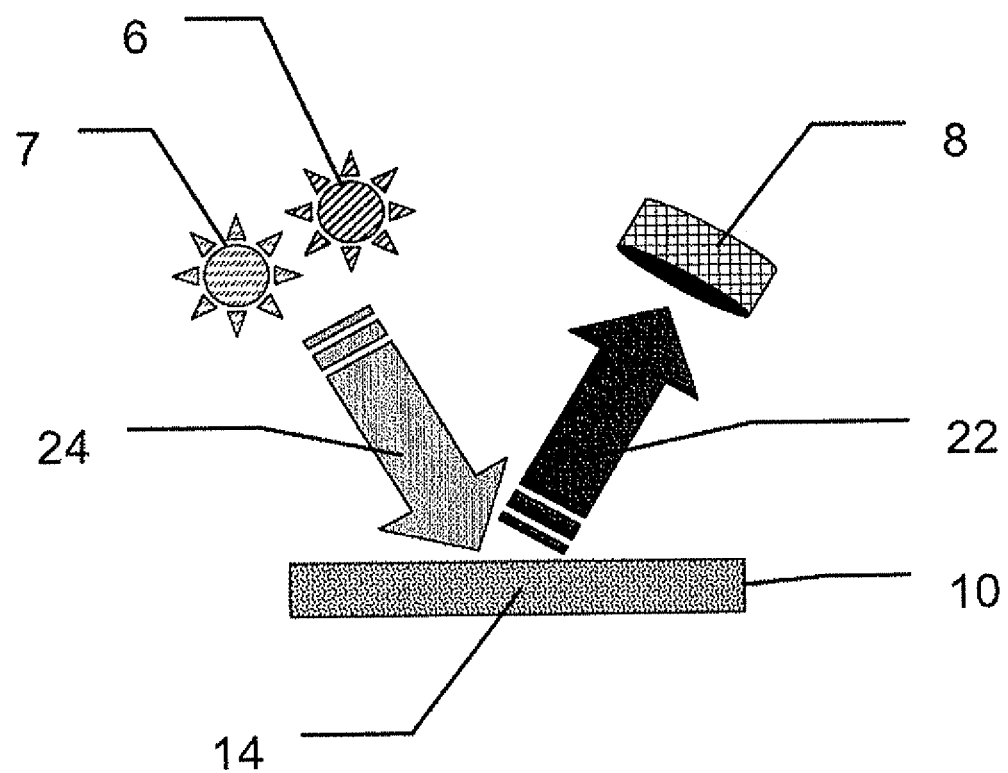
FIG. 1 is a sketch of the principles for illustrating the method for determining a measured variable of a measured medium.

FIG. 1 shows, schematically, a method for determining a measured variable of a measured medium, for example, a variable such as a pH value or a concentration of an analyte in the measured medium. In the case of this method, a first light source 6 and a second light source 7 are activated for emitting first and second light signals of different wavelength. The light signals propagate as measurement light signals on a measuring path, for example, via first light conductor 24, wherein they impinge on a matrix 10, which has at least one region 14, which contains an indicator or an indicator mixture. In the here illustrated example, the entire first, and, respectively, second, light signal emitted from the first, and, respectively, second light source 6, 7 is used as measurement light signal.

Matrix 10 is brought into contact with the measured medium, for example, by immersion. By interaction with the indicator present in the matrix 10 in the region 14, the first and second measurement light signals are transformed. Generally, the transformation of a light signal by an indicator includes especially the absorption of a part of the light signal by the indicator. The transformed light signal can be, on the one hand, a transmission signal weakened in its intensity due to the absorption, on the other hand, however, also a light signal, which the indicator emits as a luminescence signal due to excitation by the absorbed light. Which type of transformed light signal is detected, depends, for example, on the choice of the indicator, choice of the detector and the orientation of the detector 8 relative to the signal path.

The wavelength of the first and second light signal is matched to the choice of the indicator: For example, the absorption spectrum of the indicator can have a first, and a second, wavelength range, in which the measured variable, e.g. the pH value, influences the absorption spectrum in different manner. This is, for example, the case for a so-called pH indicator, whose protonated and deprotonated forms have absorption maxima at different wavelengths. An example of such a indicator is bromine thymol blue, which will be yet more exactly explored further below in connection with FIGS. 2 and 3. In this case, the wavelength of the one light signal is selected in the first wavelength range, e.g. in the region of the absorption maximum of the protonated form, and the wavelength of the other light signal in the second wavelength range, e.g. in the region of the absorption maximum of the deprotonated form.

In a variant, the absorption spectrum of the indicator can also have a first wavelength range, in which the measured variable influences the absorption spectrum, e.g. an absorption maximum dependent on the pH value, and a second wavelength range, in which the measured variable does not influence the absorption spectrum, e.g. when an isosbestic point is present. The wavelength of the first light signal can then be selected in the first wavelength range and the wavelength of the second light signal in the second wavelength range, e.g., at the isosbestic point.

As a rule, the first, and the second, light signals must not be strongly monochromatic. If, as second light signal, the wavelength of the isosbestic point is selected, it is, however, of advantage to use monochromatic light.

The transformed first and second measurement light signals reach on the measuring path, for example, through second light conductor 22, the detector 8, which registers the total intensity of the first and second transformed measurement light signals, thus the sum of the intensities of the transformed first and second measurement light signals.

In the schematic representation in FIG. 1, the light sources 6, 7 and the detector 8 are located on the same side of the matrix 10. In the case, in which the change of the intensity of the light signals due to absorption by the indicator are to be registered by the detector 8, it is advantageous to provide in, or in the vicinity of, the matrix 10 additional means, which strengthen the reflection of the light signals on the matrix 10. For example, the matrix 10 can have on its side facing away from the light sources 6, 7 and the detector 8 a reflecting layer, for example, of aluminum. Additionally, or alternatively, the matrix 10 can also contain light scattering particles integrated into the matrix 10, for example, silica gel or rutile powder with a particle diameter in the μm-range. In case it is provided, that the detector 8 receives a luminescence signal emitted by the indicator, an amplification of the reflection on the matrix 10 is not absolutely necessary, since luminescence signals are emitted uniformly in all spatial directions. It is, however, advantageous also, in this case, to provide a reflecting layer, in order that a larger part of the emitted luminescence signal reaches the detector 28.

The method explained here and in the following on the basis of an embodiment, in the case of which the indicator or the indicator mixture is present in a matrix 10, can alternatively also be performed in a manner such that the measured medium is mixed with the indicator or the indicator mixture for determining the measured variable, e.g. by adding the indicator or the indicator mixture to at least one sample of the measured medium.

The intensities of the first and second light signals are modulated, respectively, by first and second, periodic signals. The total intensity of the transformed first and second light signals registered by the detector 8 is correspondingly likewise periodically modulated, i.e. the total intensity varies periodically. If, for example, a sine-like signal is selected as first and second, periodic signal, then the total intensity registered by the detector 8 likewise exhibits a sine-like curve. The total intensity is, in such case, shifted relative to the first, and the second, periodic signal phase-. In the following, this is explained more exactly on the basis of the already mentioned example of determining the pH value of a measured medium by means of the acid/base indicator bromine thymol blue.

It is known to those skilled in the art, that bromine thymol blue has different absorption spectra for different pH values, since the deprotonated and protonated forms of bromine thymol blue possess different absorption maxima. Thus, the absorption spectrum of the deprotonated form of bromine thymol blue has an absorption maximum at 620 nm, which differs clearly from the absorption maximum of the protonated form at 430 nm. Depending on pH value, the concentration ratio changes in favor of the protonated, or the deprotonated, form, and, correspondingly, the intensity ratio of the two absorption maxima also changes. The absorption spectrum of bromine thymol blue includes two isosbestic points, one at 320 nm and the other at 500 nm.

Selected as wavelength of the first light signal is the wavelength of the absorption maximum of the protonated form, thus 430 nm, and as wavelength of the second light signal the wavelength of the absorption maximum of the deprotonated form, 620 nm. The intensity of the first light signal and the intensity of the second light signal are modulated, respectively, by a first, and a second, periodic signal, in the illustrated example a sine-like signal.

Figure 2:
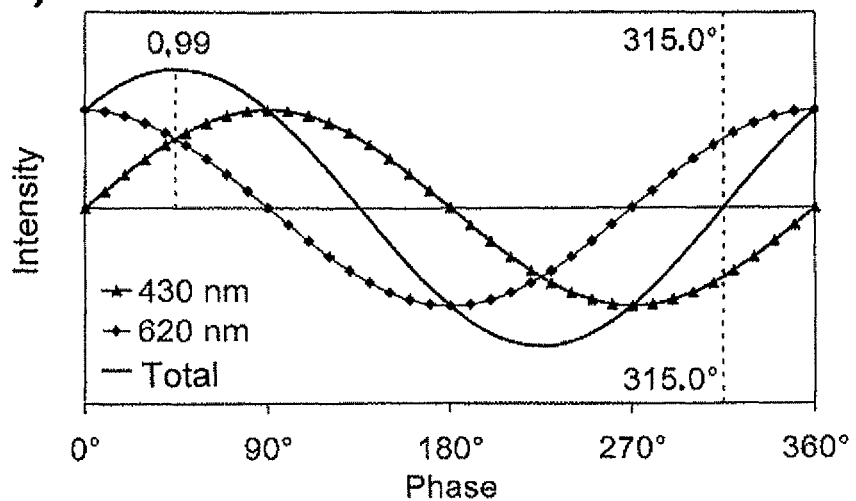
FIG. 2 is a) a graph of the intensities of the modulated first and second measurement light signals emitted from the first and second light source, as well as their total intensity; and
b) a graph of the modulated intensities of the first and second measurement light signals transformed by interaction with the indicator bromine thymol blue, as well as their total intensity.
Figure 2:
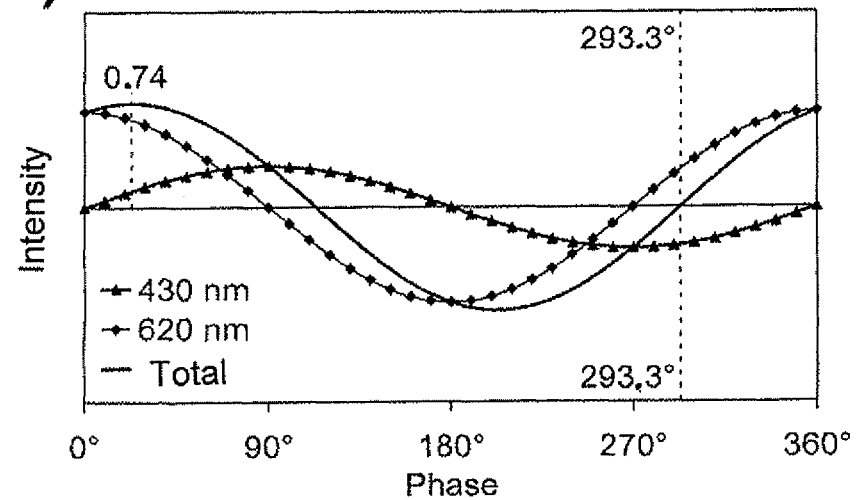

FIG. 2 $a$) is a graph of the modulated intensities of the first measurement light signal (430 nm, triangles) and the second measurement light signal (620 nm, diamonds), as well as the total intensity of the first and second measurement light signals (solid line) as a function of the phase the modulated intensity of the first measurement light signal. In the illustrated example, frequency and amplitude of the modulated sine-like signals are equal; the phase difference the modulated sine-like signals amounts to 90°, or $\pi/2$. In the illustrated example, it is furthermore assumed, that the intensities of the first and second light signals are essentially modulated by no additional signals. The modulated intensity of the first light signal and the modulated intensity of the second light signal possess thus the same frequency and amplitude and a phase difference of 90°, or π/2. The modulated total intensity is correspondingly likewise a sine-like curve.

Presented in FIG. 2 b) as a function of the phase of the first modulated measurement light signal are, by way of example, the intensities of the first measurement light signal and the second measurement light signal transformed by interaction with an indicator. Since the intensities of the radiated measurement light signals are modulated by a sine-like periodic signal, the intensities of the transformed measurement light signals and correspondingly also their total intensity exhibit likewise a sine-like, periodic curve. In the illustrated example, the intensities of both measurement light signals change due to absorption by bromine thymol blue in different manner, and, indeed, as a function of the pH value. The first measurement light signal with the wavelength of 430 nm is, in the case of the particular pH value of this example, clearly less strongly absorbed than the second measurement light signal of wavelength 620 nm, which is expressed in a clearly increased decrease of the amplitude of the intensity of the transformed second measurement light signal compared with the decrease of the amplitude of the intensity of the transformed first measurement light signal. The total intensity exhibits a phase difference relative to the individual intensities of the transformed first, or the transformed second measurement light signal. This phase difference is identical with the phase difference of the total intensity relative to the individual intensities of the radiated first, or second measurement signal and with the phase difference of the total intensity relative to the first periodic signal modulating the intensity of the first light signal emitted from the first light source, or the second, periodic signal modulating the intensity of the second light signal emitted from the second light source. For the following considerations, it is assumed, purely by way of example, that this phase difference is determined by ascertaining the phase difference between the total intensity of the transformed measurement light signals and an individual intensity of one of the transformed measurement light signals.

This phase difference depends on the ratio of the intensities, or the amplitude ratio, of the modulated intensities of the individual transformed measurement light signals, as is shown in the following. In such case, it is assumed, that the individual signals superimpose additively:

$$A_{measurement} \cdot \sin(\phi_{measurement}) = A_{\lambda 1} \cdot \sin(\phi_{\lambda 1}) + A_{\lambda 2} \cdot \sin(\phi_{\lambda 2}), \text{ and} \quad (1)$$

$$A_{measurement} \cdot \cos(\phi_{measurement}) = A_{\lambda 1} \cdot \cos(\phi_{\lambda 1}) + A_{\lambda 2} \cdot \cos(\phi_{\lambda 2}) \quad (2)$$

wherein $A_{measurement}$ stands for the amplitude of the total intensity, $\phi_{measurement}$ for the phase angle of the total intensity, $A_{\lambda 1}$ for the amplitude of the intensity of the transformed first sine-like modulated measurement light signal, $A_{\lambda 2}$ for the amplitude of the intensity of the transformed second sine-like modulated measurement light signal, $\phi_{\lambda 1}$ for the phase angle of the transformed first measurement light signal and $\phi_{\lambda 2}$ for the phase angle of the transformed second measurement light signal.

Established as reference variable is here the phase angle $\phi_{\lambda 1}$ of the transformed first measurement light signal, i.e.

$$\phi_{\lambda 1} = 0.$$

Of course, equally selectable as reference variable is the phase angle $\phi_{\lambda 2}$ of the transformed second measurement light signal.

Using the first choice, there results from the equations (1) and (2):

$$A_{measurement} \cdot \sin(\phi_{measurement}) = A_{\lambda 2} \cdot \sin(\phi_{\lambda 2}), \text{ and} \quad (3)$$

$$A_{measurement} \cdot \cos(\phi_{measurement}) = A_{\lambda 1} + A_{\lambda 2} \cdot \cos(\phi_{\lambda 2}), \quad (4)$$

Division of equation (4) by equation (3) yields:

$$\cot(\varphi_{measurement}) = \cot(\varphi_{\lambda 2}) + \frac{1}{\sin(\varphi_{\lambda 2})} \cdot \frac{A_{\lambda 1}}{A_{\lambda 2}}. \quad (5)$$

From equation (5), it follows that the phase difference between the transformed first measurement light signal as reference point and the total intensity of the transformed first and second measurement light signals registered by the detector in the case of constant phase difference between the first and second, periodic signals depends exclusively on the quotient of the amplitudes (and therewith on the intensity ratio of the transformed first and second measurement light signals).

By means of equation (5), consequently, the amplitude ratio of the modulated intensity of the transformed first and second measurement light signals can be ascertained. With knowledge of the indicator concentration in the measured medium, or in the matrix 10, the sought measured variable, in the present example the pH value, can be determined, for example, by comparing the ascertained amplitude ratio with calibration data ascertained for the particular indicator concentration.

As is known, the following holds for the amplitude ratio of the modulated intensities of the transformed first and second measurement light signals:

$$\frac{A_{\lambda 1}}{A_{\lambda 2}} = \frac{A_{\lambda 1}^0 \cdot T_{\lambda 1}^{Ind}}{A_{\lambda 2}^0 \cdot T_{\lambda 2}^{Ind}}, \quad (6)$$

wherein $A_{\lambda 1}^0$ is the amplitude of the intensity of the radiated first measurement light signal before interaction with the indicator, $A_{\lambda 2}^0$ the amplitude of the intensity of the radiated second measurement light signal before interaction with the indicator, $T_{\lambda 1}^{Ind}$ the transmission of the indicator for light of the wavelength of the first measurement light signal and $T_{\lambda 2}^{Ind}$ the transmission of the indicator for light of the wavelength of the second measurement light signal. The transmission of the indicator for the first, or the second, measurement light signal depends according to the Lambert-Beer law exponentially on the radiated path length d and the absolute concentration of the absorbing indicator form, i.e., in the present case, the concentration $c_1^{Ind}$ of the deprotonated form of bromine thymol blue, and the concentration $c_2^{Ind}$ of the corresponding protonated form, respectively:

$$T_{\lambda 1}^{Ind} = \frac{A_{\lambda 1}}{A_{\lambda 1}^0} = 10^{-(\varepsilon_{\lambda 1} + C_1^{Ind} \cdot d)}, \text{ or } T_{\lambda 2}^{Ind} = \frac{A_{\lambda 2}}{A_{\lambda 2}^0} = 10^{-(\varepsilon_{\lambda 2} + C_2^{Ind} \cdot d)}. \quad (7)$$

The variables $\varepsilon_{\lambda 1}$ and $\varepsilon_{\lambda 2}$ are constants characteristic for the particular indicator form and are referred to as extinction coefficients.

In order to eliminate the influence of a non constant indicator concentration, for example, because of bleaching or leaching or, in the case of replacement of the matrix 10, supplementally, the amplitude of the total intensity of the transformed first and the transformed second measurement light signal can be ascertained. In such case, it is assumed that the distance d passed through by the measurement light signal remains constant and is additionally equally large for the first and second measurement light signals. By means of equations (3) and (4), the absolute values of the amplitudes $A_{\lambda 1}$ and $A_{\lambda 2}$ can be calculated from the values $A_{measurement}$ and $\phi_{measurement}$. From this, the associated absorption values $OD_{\lambda 1}$ and $OD_{\lambda 2}$ for the two indicator forms can be calculated as follows:

$$OD_{\lambda 1} = -lg(T_{\lambda 1}) = -lg\left(\frac{A_{\lambda 1}}{A_{\lambda 1}^0}\right) = \varepsilon_{\lambda 1} \cdot c_1^{Ind} \cdot d \qquad (8)$$

and $$OD_{\lambda 2} = -lg(T_{\lambda 2}) = -lg\left(\frac{A_{\lambda 2}}{A_{\lambda 2}^0}\right) = \varepsilon_{\lambda 2} \cdot c_2^{Ind} \cdot d.$$

The quotient, or the ratio, of the absorption values represents a variable independent of the concentration of the indicator and reflectes alone the concentration ratio of the two forms of the indicator:

$$\frac{OD_{\lambda 1}}{OD_{\lambda 2}} = \frac{\varepsilon_{\lambda 1} \cdot c_1^{Ind}}{\varepsilon_{\lambda 2} \cdot c_2^{Ind}}. \qquad (9)$$

From the quotient of the absorption values, thus, independently of a changing indicator concentration, i.e. a changing total concentration of all present indicator forms, for example, again, by comparison with corresponding calibration data, the measured variable, in the here discussed example the pH value, can be ascertained.

The measuring of the amplitude $A_{measurement}$ of the total intensity of the transformed first and the transformed second measurement light signals can occur by means of a simple measuring apparatus, since $A_{measurement}$ in the case of a sufficient indicator concentration lies within an interval $$0.1 \cdot (A_{\lambda 1}^0 + A_{\lambda 2}^0) < A_{Mess} < 0.9 \cdot (A_{\lambda 1}^0 + A_{\lambda 2}^0) \qquad (10)$$

In the case of conventional ratiometric methods, as such initially were described, the measuring of the individual intensities of the transformed light signals is necessary. This requires an essentially higher accuracy of measurement than the determining of the total amplitude $A_{measurement}$. This is true especially in the case of presence of a pH value or an analyte concentration, in the case of which the indicator is almost completely present in one form. If the indicator is present, for example, almost exclusively in the protonated form, then the amplitude of the intensity of the transformed first measurement light signal $A_{\lambda 1}$ is only minimally smaller than the amplitude $A_{\lambda 1}^0$ of the intensity of the first measurement light signal before the interaction with the indicator, while the intensity of the transformed second measurement light signal has a strongly lessened amplitude $A_{\lambda 2}$. If, in this case, the individual intensities of the transformed measurement light signals are measured, this leads to a relatively large measurement error, while the measuring of the amplitude of the total intensity of the transformed measurement light signals in the case of equal apparatus complexity is burdened with a clearly smaller measurement error. Since, in contrast with the conventional ratiometric methods, no measurements of amplitudes with $A \approx 0$, or $A \approx A^0$, must occur, the determining of the total amplitude $A_{measurement}$ can occur with clearly lesser apparatus complexity.

The determining of the phase difference $\phi_{measurement}$ and the amplitude $A_{measurement}$ of the total intensity can occur at the same time, so that a continuous measuring is possible without spatial or time separation of the measurement channels of the first and second measurement light signals and without the use of optical filters. Also this is an advantage compared with the initially described methods known from the state of the art.

In the case of equal absolute error of the amplitudes, or intensity, measurement and a typical error of, for example, 0.025° in the determining of the phase shift, additionally, the amplitudes of the intensities of the first and second measurement light signals can be reduced markedly compared with the individual determining of the measurement light intensities in the case of the conventional ratiometric methods, without enlarging the total measurement error. This lessening of the measurement light intensity has the advantage that photobleaching of the indicator is reduced. The life of a sensor working according to the described method with an indicator containing matrix 10 would, in this way, be lengthened relative to the life of a sensor working according to the conventional ratiometric method.

Figure 3:
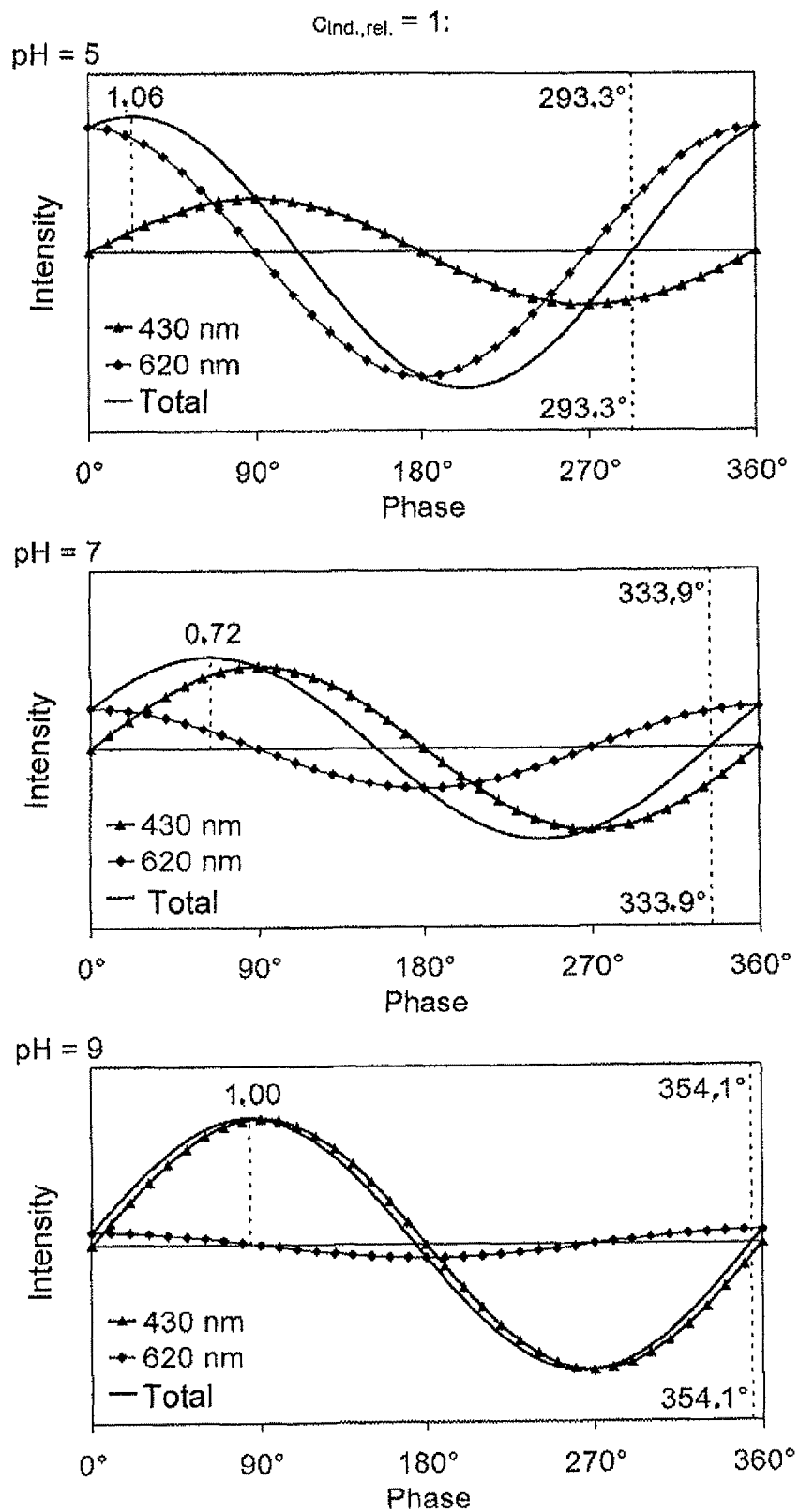
FIG. 3 are graphs of the total intensity of first and second measurement light signals transformed by interaction with bromine thymol blue ascertained in a simulation in the case of different pH values.

FIG. 3 presents a series of graphs of the total intensity (solid line) ascertained in a simulation for a first measurement light signal of the wavelength 430 nm (triangles) transformed by interaction with bromine thymol blue and for a likewise transformed second measurement light signal of the wavelength 620 nm (diamonds) in the case of pH values of 5, 7 and 9. The intensities of the transformed measurement light signals are, in each case, modulated with a sine-like signal, wherein in the present case both the sine-like signals modulating the radiated measurement light signals, and, correspondingly, the modulated intensities of the transformed measurement light signals, have equal frequencies and equal amplitudes. The phase difference between the modulated sine-like signals, and correspondingly also the phase difference between the two modulated transformed measurement light signals amounts in the illustrated example to 90°, or $\pi/2$.

As reference variable for the determining of the phase difference of the total intensity of the transformed light signals, the phase angle of the transformed first measurement light signal (430 nm) is selected. Correspondingly, the zero passing of the sine function modulating the first light signal is selected as the origin of the coordinate system of the here illustrated graphs. The phase shift of the total intensity referenced to this origin is shown as a dashed line in all graphs.

It is easily evident that, with rising pH value, the intensity ratio of the transformed signals changes. Correspondingly, the amplitude ratios of the transformed modulated measurement light signals change and, thus, also the phase shift of the total intensity referenced to the selected origin.

An analogous method can be used also for determining concentration of other analytes, such as e.g. the concentration dissolved in the measured medium of carbon dioxide, oxygen, chlorine, hydrogen, ammonia, nitrate-, ammonium-, chloride-, fluoride-, phosphate-, sulfate, cyanide-, alkali- and alkaline earth ions, of heavy metal containing, ionic compounds, or also of biomolecules, especially proteins or substances produced by microorganisms. For this, numerous indicators known from the state of the art, e.g. chromo-ionophores or markers known from biosensors, can be used.

As an example, the following will describe the determining of the concentration of potassium ions in greater detail. For this, the matrix 10 is embodied as a membrane, which contains, besides a K⁺ selective, neutral carrier, also a H⁺ selective membrane chromo-ionophore. If the measured medium contains dissolved potassium ions, these diffuse into the membrane and are there complexed by the carrier. Since the carrier is uncharged, the complex correspondingly possesses a positive charge. For charge equalization of the membrane, H⁺ ions are given off in the measured medium, which leads to a change of the pH value in the membrane. This pH value change expresses itself correspondingly as a change of the absorption spectrum of the membrane chromo-ionophore. For example, the matrix 10 can be formed of a PVC-membrane with plasticizer additions, which contains as K⁺ selective carrier a hexaester of calix[6]arene and the H⁺ selective chromo-ionophore ETH 2439. The absorption spectrum of this chromo-ionophore includes an absorption maximum at, for instance, 670 nm, whose intensity depends in the described manner on the K⁺ concentration present. At 575 nm, the system possesses an isosbestic point.

For determining the K⁺ concentration, the matrix 10 is brought in contact with the measured medium and a first measurement light signal with a wavelength of 670 nm and a first periodic signal modulating the intensity of the first measurement light signal and a second measurement light signal with a wavelength of 575 nm and a second, periodic signal modulating the intensity of the second measurement light signal are radiated in. The total intensity of the measurement light signals transformed by absorption by the indicator is registered by means of a detector, for example, a broadband photodetector. The intensity of the first measurement light signal at 670 nm is influenced by the K⁺ concentration in the measured medium, while the intensity of the second measurement light signal at 575 nm, the isosbestic point, is independent of the K⁺ concentration. From the phase difference of the detected total intensity of the transformed measurement light signals relative to the first or second, periodic signal as reference point, the K⁺ concentration is determined according to the earlier described method, in given cases, with additional determining of the amplitude of the total intensity of the transformed first and second measurement light signals.

In analogous manner, the method can be applied by detecting, instead of an absorption response of an indicator, the luminescence response of an indicator to the radiated measurement light signals. In this case, the indicator is excited with two measurement light signals to luminesce, especially to fluoresce. As earlier described, the intensities of the exciter signals are, in each case, modulated by a periodic signal, wherein a phase difference exits between the two periodic signals. The total intensity of the measurement light signals emitted, i.e. transformed, by the indicator is detected and the phase difference of the total intensity relative to the first, or the second, periodic signal is determined. This phase difference is, as in the case of the earlier considered absorption measurements, a measure for the amplitude ratio of the intensity of the luminescence signals in the case of excitation with the first and second measurement light signals, and therewith a measure for the concentration ratio, in which two different forms of the indicator are present. This concentration ratio is, in turn, a measure for the pH value, or the analyte concentration.

In the case of evaluation of luminescence measurements at small indicator concentrations, a linear relationship between the intensity of the transformed measurement light signal, thus the luminescence intensity, and the concentration of the luminescing species can be assumed with good approximation, so that also changes of the indicator concentration during the life of a sensor working according to this method only insignificantly influence the accuracy of measurement. In order to eliminate completely the influence of a non constant indicator concentration, as for the absorption measurements earlier described, supplementally, the amplitude of the total intensity of the transformed measurement light signals, i.e. in the case of the luminescence-measuring of the luminescence signals, $A_{measurement}$, can be ascertained.

From the relationship between the amplitudes $A_{\lambda 1'}$ and $A_{\lambda 2'}$ of the individual transformed measurement light signals and the concentration of the first indicator form luminescing in the case of excitation with the first measurement light signal and the second indicator form luminescing in the case of excitation with the second measurement light signal, respectively, $$A_{\lambda 1'} = A_{\lambda 1}^0 \cdot \Theta_1 \cdot (1 - 10^{-\epsilon_{\lambda 1} \cdot c_1^{Ind} \cdot d}), \text{ or } A_{\lambda 2'} = A_{\lambda 2}^0 \cdot \Theta_2 \cdot (1 - 10^{-\epsilon_{\lambda 2} \cdot c_2^{Ind} \cdot d}) \tag{11}$$

with $\Theta_1$ and $\Theta_2$ as quantum yield and in the case of knowledge, or reference measurement, of $A_{\lambda 1}^0$ and $A_{\lambda}^0$, an absorption value $OD_{\lambda 1}$ for the excitation with the first measurement light signal, and an absorption value $OD_{\lambda 2}$ for the excitation with the second measurement light signal, respectively, can be ascertained, which, in each case, depends linearly on the concentration of the respective indicator form:

$$OD_{\lambda 1} = -lg\left(1 - \frac{A_{\lambda 1'}}{A_{\lambda 1}^0 \cdot \Theta_1}\right) = \epsilon_{\lambda 1} \cdot c_1^{Ind} \cdot d, \tag{12}$$

and $$OD_{\lambda 2} = -lg\left(1 - \frac{A_{\lambda 2'}}{A_{\lambda 2}^0 \cdot \Theta_2}\right) = \epsilon_{\lambda 2} \cdot c_2^{Ind} \cdot d.$$

The quotient of the absorption values represents a variable independent of the concentration of the indicator and reflects alone the concentration ratio of the two luminescing forms of the indicator. From the quotient of the absorption values, thus, independently of a changing indicator concentration, i.e. a changing total concentration of all present indicator forms, for example, by comparison with corresponding calibration data, the measured variable, e.g. an analyte concentration, or the pH value in the measured medium, can be ascertained.

For example, for determining the pH value of a measured medium, there can be used as indicator 1-hydroxypyrene-3, 6,8-trisolfonic acid N-cetyl-N,N,N-trimethyl ammonium salt (HPTS-CTEA) contained in a sol-gel matrix. This indicator possesses two absorption maxima, whose intensity depends on the pH value, wherein the first at 404 nm can be associated with the deprotonated form and the second at 455 nm with the protonated form. The indicator is, as earlier described, as a component of a matrix 10, brought in contact with the measured medium. In the case of excitation of the indicator with a first periodically modulated measurement light signal having a wavelength of 404 nm and in the case of excitation with a second phase-shifted, periodically modulated measurement light signal having a wavelength of 455 nm, from the phase difference of the total intensity of the signals emitted at 510 nm, the pH value of the measured medium can be determined according to above described method.

Instead of an individual indicator as in the previously described examples of embodiments, also a mixture of a plurality of indicators can be used. For example, a mixture of two indicators can be used, wherein only one of the indicators has an absorption spectrum dependent on the pH value, or the analyte concentration, while the absorption spectrum of the second indicator is independent of the pH value, or the analyte concentration. An example of such a indicator mixture is a mixture of N-allyl-4-piperazinyl-1,8-naphthalimide (APN, also: piperazinyl-1,8-naphthalimide) and N-(2-methacryloxyethyl)benzo[k,l]thio-xanthene-3,4-dicarboximide (MBTD, also: benzothioxanthene). These indicators are co-polymerisiert with acrylamide, hydroxymethyl-methacrylate and triethyleneglycol-dimethacrylate, in order to form a matrix 10.

The absorption spectrum of APN exhibits at 393 nm an absorption maximum, whose intensity depends on the pH value. The absorption spectrum of MBTD is, as a whole, independent of the pH value and exhibits a maximum at 479 nm. In the case of excitation of the indicator mixture with a first measurement light signal with a wavelength of 393 nm and a second measurement light signal with a wavelength of 479 nm, wherein the intensities of both measurement light signals are modulated each with its own periodic signal and the two periodic signals are phase shifted relative to one another, from the phase difference of the total intensity emitted at 530 nm by the indicator mixture relative to the first, or second, periodic signal, the pH value of the measured medium can be determined according to described method.

Besides the interaction with the indicator, additional influences along the measuring path can influence the intensity of the first and second measurement light signals. Such influenced can be, for example, fluctuations of the light intensity of the first, or the second, light source, as well as absorption or refraction of the measurement light signals by substances in the measuring path, reflection on interfaces in the measuring path, for example, on cuvette windows, or a different spectral sensitivity of the detector for the first and second measurement light signals transformed by interaction with the indicator or indicator mixture. Frequently, these additional influences do not act in equal measure on the two light signals of different wavelength. Thus, absorption, refraction and reflection are wavelength dependent. Especially, the sensitivity of a photodetector is, in general, wavelength dependent. Also, the two light sources can be subject to different component fluctuations.

Thus, indeed, by the application of two measurement light signals and the application of a phase difference proportional to the intensity ratio of the measurement light signals transformed by interaction with the indicator for determining the measured variable, a part of the already initially mentioned, disturbing influences are eliminated. Those disturbing influenced, which act differently strongly on the two light signals, cannot, however, be compensated in this way.

For this reason, it is advantageous, besides the previously described signal path, which serves for determining the sought measured variable, the so-called measuring path, to provide a second signal path as reference path. In this regard, a part of the light signals emitted from the first and second light source and, in each case, modulated with a periodic signal from the measuring path are diverted and exposed on the reference path to the same influences, which also the signals on the measuring path are exposed to; however, the signals of the reference path are not brought into contact with the indicator or indicator mixture. The diverting of the reference light signals from the measuring path can occur by means of conventional methods, for example, with the assistance of a semi-transmissive mirror or some other beam divider. The reference light signals changed on the reference path can be registered by a separate detector. Another option is to register the reference light signals and the measurement light signals sequentially with the same detector.

Since the intensity of the first and second reference light signal on the reference path is changed in different manner by the additional influences, the total intensity of the reference light signals registered on the detector has a phase difference relative to the periodic signals modulating the intensity of the first and second light signals. This phase difference can be determined and used, together with the phase difference of the total intensity of the transformed first and second measurement light signals relative to the periodic signals, as ascertained on the measuring path, for the evaluation for determining the measured variable. In such case, it is sensible to refer the phase difference of the total intensity registered on the measuring path and that on the reference path to the same periodic signal. In this way, the additional influences on the measurement result can be eliminated, and a more accurate measured value obtained. The determining of the measured variable can occur by means of an evaluating unit, which can comprise especially an electronic data processing unit, e.g. a microcontroller or a computer.

The intensity ratio of the light signals emitted from the light sources can be so set that the phase difference registered on the reference path relative to one of the periodic signals has a constant value. The phase difference ascertained on the reference path is then exclusively caused by the different transformation by the indicator, or by the indicator mixture, at the different wavelengths of the two radiated light signals.

Figure 4:
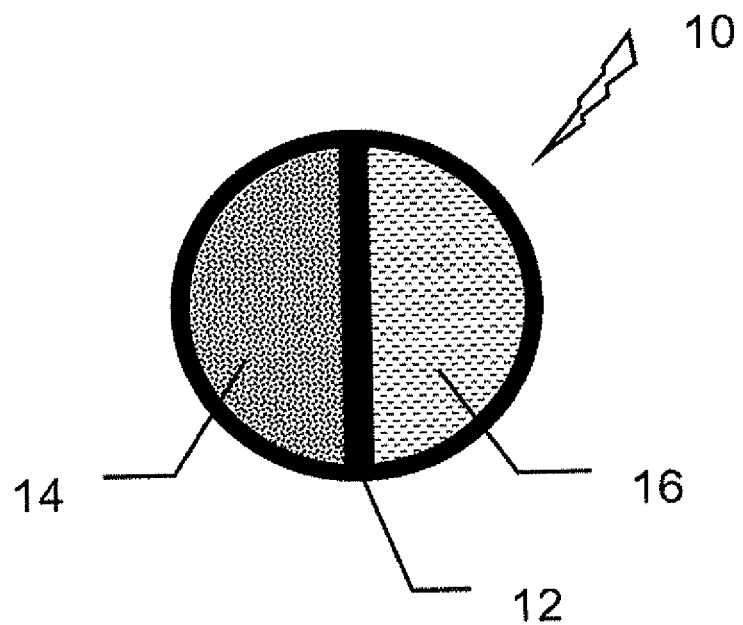
FIG. 4 is a schematic representation of a matrix with a first region, which includes an indicator, and a second, indicator free region.

An apparatus for performing the method includes a matrix 10, as shown in FIG. 4. Secured in a support 12 transparent for the used wavelengths is a membrane, which has two regions 14, 16 separated from one another by a support strut. The first region 14 includes the indicator or the indicator mixture, while the second region 16 contains no indicator. The signal paths of the apparatus can by way of optical means, especially by way of optical elements, such as mirrors, lenses, beam dividers or optical fibers, be so embodied that the light signals of the measuring path impinge on the matrix 10 in the first region 14 and the light signals of the reference path impinge on the matrix 10 in the second region 16.

Figure 5:
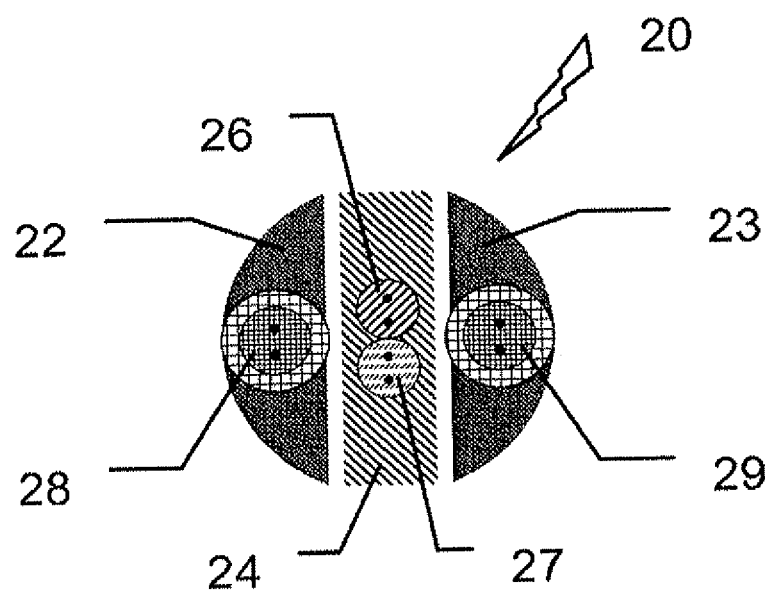
FIG. 5 is a schematic representation of a cross section through a measuring probe having a measuring- and a reference path.
Figure 6:
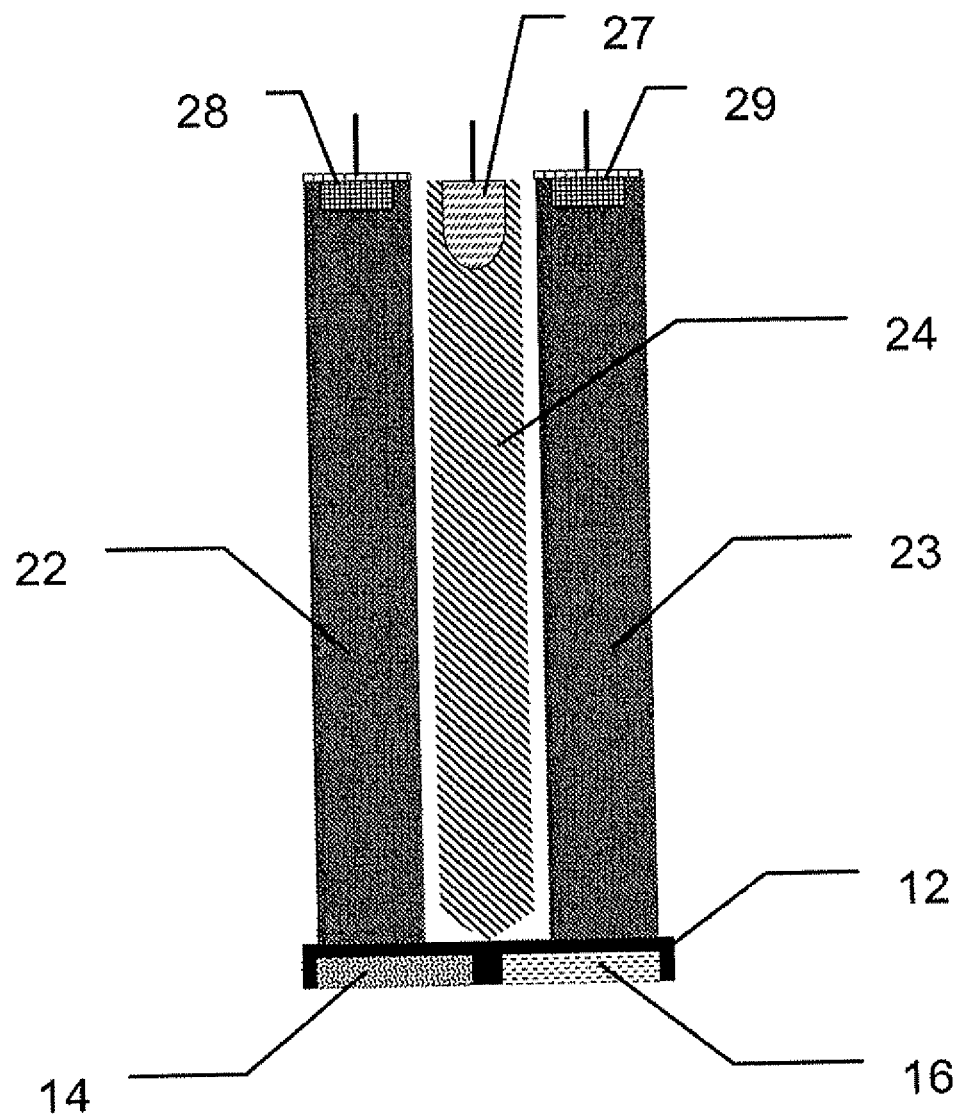
FIG. 6 is a schematic representation of a longitudinal section through the measuring probe shown in FIG. 5.

The immobilizing of the indicator in a matrix 10 and the arrangement of the light sources as well as of the one or more detectors on the same side of the matrix 10, as indicated in FIG. 1, permits embodying the apparatus for performing the method as a sensor having a measuring probe 20 immersible in the measured medium. FIG. 5 shows a schematic representation of a cross section through such a measuring probe 20 having a measuring- and a reference path. FIG. 6 shows a schematic representation of a longitudinal section through the measuring probe 20.

Serving as light sources are two light emitting diodes 26, 27 arranged next to one another. The light sources do not have to be arranged in the measuring probe 20. It is instead also possible to arrange the light sources spatially removed from the measuring probe 20 and to couple the light signals via light conductors into the measuring probe 20. It is, moreover, feasible to use, instead of two light emitting diodes 26, 27 emitting the light signals of different wavelengths, a dual light emitting diode emitting the two wavelengths. A first light conductor 24 is connected in such a manner with the light emitting diodes 26, 27, in given cases via optical elements, that light signals of the light emitting diodes 26, 27 are coupled into the light conductor 24. The light emitting diodes 26, 27 are fed from an electrical current source (not shown). The electrical current source is correspondingly controlled for modulating periodic signals onto the intensities of the signals emitted from the light emitting diodes. Apparatuses for this as well as alternative apparatuses for the modulation of the light emitting diode signals are known to those skilled in the art.

The light conductor 24 is arranged at its end away from the light emitting diodes 26, 27 in such a manner relative to the support 12 of the matrix 10 that the two light signals of the light emitting diodes 26, 27 impinge both on the indicator containing region 14 as well as also on the indicator free region 16 of the matrix 10. In this regard, the existing divergence of the light signals can be utilized; however, also optical elements such as beam dividers, lenses or mirrors can be applied for the beam deflection. It is also feasible to fashion the light conductor 24 from a plurality of optical fibers, which conduct the light signals partly to the indicator containing region 14 and partly to the indicator free region 16.

The two regions 14 and 16 of the matrix 10 are connected via light conductors 22 and 23 with two photodetectors 28 and 29 integrated in the measuring probe 20. As in the case of the light sources 26, 27, the photodetectors 28, 29 can also be arranged spatially removed from the measuring probe 20. In the case of luminescence measurements, there is arranged in the signal path between the matrix 10 and the photodetectors 28 and 29 an optical filter (not shown), which filters out light from the measuring-, or reference path reflected on the matrix and allows to pass only the transformed measuring-, or reference light signals.

The detector signals of the photodetectors 28, 29 are evaluated by an evaluating unit (not shown), which is especially designed to determine the phase difference between the detected total intensity and the periodic signal modulating the first or second light signal intensity. Such apparatuses for determining phase difference are known to those skilled in the art. The evaluating unit matches the phase difference with a pH value, or with an analyte concentration. This matching can occur with the assistance of stored calibration data. For this, the evaluating unit includes especially a data processing unit, for example, a microcontroller or a PC.

The invention claimed is:

1. A method for determining a measured variable of a measured medium, comprising the steps of:
    bringing the measured medium in contact with an indicator or an indicator mixture, whose absorption spectrum has a first, and a second, wavelength range, which essentially do not overlap;
    activating a first light source for emitting a first light signal with a wavelength from the first wavelength range and a second light source for emitting a second light signal with a wavelength from the second wavelength range, the intensity of the first light signal being modulated by a first periodic signal, and the intensity of the second light signal being modulated by a second, periodic signal, the first periodic signal and the second periodic signal having equal frequencies;
    at least a part of the first light signal and at least a part of the second light signal propagate as first and second measurement light signals along a measuring path and are transformed on the measuring path by optical interaction with the indicator or the indicator mixture;
    registering a total intensity of the transformed first and second measurement light signals
    providing the first periodic signal with a first phase difference relative to the second, periodic signal;
    ascertaining a second phase difference between the total intensity of the transformed first and second measurement light signals and the first or the second periodic signal; and
    determining the measured variable with application of the second phase difference.

2. The method as claimed in claim 1, wherein:
the step of ascertaining the second phase difference between the total intensity of the transformed first and second measurement light signals and the first or the second periodic signal comprises: determining a phase difference between the intensity of the first measurement light signal and the total intensity of the transformed first and second measurement light signals or as determining a phase difference between the intensity of the second measurement light signal and the total intensity of the transformed first and second measurement light signals.

3. The method as claimed in claim 1, wherein:
the step of ascertaining the second phase difference between the total intensity of the transformed first and second measurement light signals and the first or the second periodic signal comprises: determining a phase difference between the intensity of the first transformed measurement light signal and the total intensity of the transformed first and second measurement light signals or determining a phase difference between the intensity of the transformed second measurement light signal and the total intensity of the transformed first and second measurement light signals.

4. The method as claimed in claim 1, wherein:
the absorption spectrum of the indicator or the indicator mixture is influenced in the first wavelength range and in the second wavelength range by the measured variable to be determined.

5. The method as claimed in claim 1, wherein:
the emission spectrum of the indicator or the indicator mixture is influenced by the measured variable to be determined as a function of excitation in the first wavelength range and in the second wavelength range.

6. The method as claimed in claim 1, wherein:
the absorption spectrum of the indicator or the indicator mixture is influenced in the first wavelength range by the measured variable to be determined and is not influenced in the second wavelength range by the measured variable to be determined.

7. The method as claimed in claim 1, wherein:
the emission spectrum of the indicator or the indicator mixture is influenced by the measured variable to be determined as a function of excitation in the first wavelength range, and is not influenced by the measured variable to be determined as a function of excitation in the second wavelength range.

8. The method as claimed in claim 6, wherein:
the second wavelength range corresponds to an isosbestic point of the indicator or of the indicator mixture.

9. The method as claimed in claim 1, further comprising:
registering the total intensity of the transformed first and second measurement light signals is registered with a single detector.

10. The method as claimed in claim 1, wherein:
the intensity of each of the first, and second light signal being modulated by a sine-like periodic signal.

11. The method as claimed in claim 10, further comprising:
ascertaining a ratio of the amplitudes of the intensities of the transformed measurement light signals from the second phase difference.

12. The method as claimed in claim 10, further comprising:
determining the amplitude of the total intensity of the transformed first and second measurement light signals and ascertaining therefrom a ratio of absorption values of the transformed measurement light signals.

13. The method as claimed in claim 10, wherein:
the first sine-like periodic signal modulating the intensity of the first light signal and the second sine-like periodic signal modulating the intensity of the second light signal have a fixed phase difference.

14. The method as claimed in claim 1, wherein:
the first and second measurement light signals are changed by additional influences on the measuring path
at least a further part of the first light signal emitted by the first light source as a first reference light signal and at least a further part of the second light signal emitted by the second light source as a second reference light signal are exposed on a reference path to the same additional influences, so that the intensity of the first and second reference light signals are changed by the additional influences; and
on the reference path, the first, and the second, reference light signals are not allowed to interact with the indicator or the indicator mixture.

15. The method as claimed in claim 14, wherein:
the additional influences comprise especially fluctuations of light intensity of the first and/or second light source, absorption and/or refraction of the light signals by substances in the measuring path and/or in the reference path, reflection on interfaces in the measuring path and/or in the reference path or a different sensitivity of the detector to the transformed first and the transformed second measurement light signals and/or the changed first and the changed second reference light signal or the incidence of stray light.

16. The method as claimed in claim 14, further comprising:
registering the total intensity of the first and second changed reference light signal with a detector, and
ascertaining the phase difference of the total intensity of the transformed first and second reference light signal relative to the first periodic signal, or the phase difference of the total intensity of the transformed first and second reference light signal relative to the second, periodic signal and determining the measured variable taking into consideration the ascertained phase difference, together with the phase difference of the total intensity of the transformed first and second measurement light signals relative to the first periodic signal or the phase difference of the total intensity of the transformed first and second measurement light signals relative to the second periodic signal.

17. The method as claimed in claim 14, further comprising:
registering the total intensity of the first and second changed reference light signal with a detector and
ascertaining the amplitude of the total intensity of the changed first and second reference light signal together with the phase difference of the total intensity of the changed first and second reference light signal relative to the first periodic signal, or the phase difference of the total intensity of the changed first and second reference light signal relative to the second periodic signal and
taking into consideration, the amplitude and the phase difference of the total intensity of the transformed first and second measurement light signals relative to the first periodic signal or the phase difference of the total intensity of the transformed first and second measurement light signal relative to the second periodic signal for determining the measured variable.

18. The method as claimed in claim 14, further comprising:
selecting the intensity of the first light signal and the intensity of the second light signal are selected relative to one another in such a manner that the phase difference between the total intensity of the changed first and second reference light signal and the first periodic signal or the phase difference between the total intensity of the changed first and second reference signal and the second periodic signal is constant.

19. The method as claimed in claim 14 further comprising:
selecting the intensity of the first light signal and the intensity of the second light signal relative to one another in such a manner that the amplitude of the total intensity of the changed first and second reference light signal as well as the phase difference of the said total intensity relative to the first periodic signal or the phase difference of the said total intensity relative to the second, periodic signal is constant.

20. The method as claimed in claim 1, wherein:
the measured variable is the pH value of the measured medium or the concentration of an analyte contained in the measured medium.

21. An apparatus for determining a measured variable of a measured medium, wherein the measured medium is brought in contact with an indicator or an indicator mixture, whose absorption spectrum has a first, and a second, wavelength range, which essentially do not overlap, comprising:
a first and a second light source for emitting a first, and a second, light signal;
a matrix, which contains the indicator or the indicator mixture;
at least one detector for registering the total intensity of the first and second measurement light signals transformed by optical interaction with the indicator or indicator mixture
an apparatus for producing a first phase difference between said first periodic signal modulating the intensity of said first light signals and said second periodic signal modulating the intensity of said second light signal; and
an apparatus for detecting a phase difference between the total intensity of the transformed first and second measurement light signals, as registered by said detector, and said first periodic signal, or a phase difference between said total intensity of the transformed first and second measurement light signals, as registered by said detector, and said second periodic signal.

22. The apparatus as claimed in claim 21, wherein:
said matrix includes, besides a first region, which contains said indicator or said indicator mixture, a second, indicator free region.

23. The apparatus as claimed in claim 22, wherein:
a measuring path for said first and second measurement light signals and a reference path for said first, and said second, reference light signal are provided, the first and the second reference light signal are changed on the reference path;
the measuring path comprises said first region of said matrix and said detector for registering the total intensity of the transformed first and second measurement light signals; and
said reference path comprises said second, indicator free region of said matrix and said detector, or an additional detector for registering the total intensity of the changed first and second reference light signal.

24. The apparatus as claimed in claim 21, wherein:
said first and said second light source and said detector are arranged on the same side of said matrix.

25. The apparatus as claimed in claim 21, wherein:
said matrix has reflection amplifying means.

26. The apparatus as claimed in claim 21, wherein:
said first and said second light source are integrated in a dual light emitting diode.

27. The apparatus as claimed in claim 23, further comprising:
an apparatus for detecting a phase difference between the total intensity of the changed first and second reference light signals, as registered by said detector or said additional detector, and the first, periodic signal or a phase difference between the total intensity of the changed first and second reference light signal, as registered by said detector or said additional detector, and the second periodic signal.

28. The method as claimed in claim 7, wherein:
the second wavelength range corresponds to an isosbestic point of the indicator or the indicator mixture.

29. The method as claimed in claim 1, wherein:
the step of activating the first light source for emitting a first light signal with a wavelength from the first wavelength range and the second light source for emitting a second light signal with a wavelength from the second wavelength range, the intensity of the first light signal is being modulated by a first periodic signal, and the intensity of the first signal being modulated by a first periodic signal comprises:
controlling a current source of the first light source and a current source of the second light source in such a way that the intensity of the first light signal is modulated by a first periodic signal and the intensity of the second light signal is modulated by a second periodic signal.

30. The method as claimed in claim 13, the first and second periodic signal having a fixed phase difference of 90°.

31. The apparatus as claimed in claim 25, wherein:
said reflection amplifying means comprising a reflecting layer and/or light scattering particles integrated into said matrix.

* * * * *